US010433995B2

(12) United States Patent
Argentine et al.

(10) Patent No.: US 10,433,995 B2
(45) Date of Patent: Oct. 8, 2019

(54) MOTORIZED DELIVERY SYSTEMS FOR AN ENOVASCULAR DEVICE

(71) Applicant: Medtronic Vascular, Inc., Santa Rosa, CA (US)

(72) Inventors: Jeffery Argentine, Petaluma, CA (US); Mark Rowe, Santa Rose, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 338 days.

(21) Appl. No.: 15/498,178

(22) Filed: Apr. 26, 2017

(65) Prior Publication Data

US 2018/0311059 A1 Nov. 1, 2018

(51) Int. Cl.
*A61F 2/966* (2013.01)
*A61F 2/95* (2013.01)

(52) U.S. Cl.
CPC ...... *A61F 2/966* (2013.01); *A61F 2002/9517* (2013.01)

(58) Field of Classification Search
CPC .. A61F 2/95; A61F 2/962; A61F 2/966; A61F 2002/9517; A61F 2002/9665
See application file for complete search history.

(56) References Cited

U.S. PATENT DOCUMENTS

| 9,445,928 | B2 | 9/2016 | Argentine |
| 9,486,350 | B2 | 11/2016 | Argentine |
| 2005/0149159 | A1 | 7/2005 | Andreas et al. |
| 2005/0273151 | A1 | 12/2005 | Fulkerson et al. |
| 2007/0112355 | A1 | 5/2007 | Salahieh et al. |
| 2007/0168014 | A1 | 7/2007 | Jimenez et al. |
| 2009/0018553 | A1 | 1/2009 | McLean et al. |
| 2009/0099638 | A1 | 4/2009 | Grewe |
| 2010/0036472 | A1 | 2/2010 | Papp |
| 2010/0168756 | A1 | 7/2010 | Dorn et al. |
| 2010/0174290 | A1 | 7/2010 | Wuebbeling et al. |
| 2011/0282425 | A1 | 11/2011 | Dwork |
| 2012/0053574 | A1 | 3/2012 | Murray, III et al. |
| 2012/0209317 | A1 | 8/2012 | Oepen |

(Continued)

FOREIGN PATENT DOCUMENTS

WO 2007/022395 A1 2/2007

OTHER PUBLICATIONS

International Search Report and Written Opinion dated Jun. 21, 2018 in corresponding European Patent Application No. PCT/US2018/026839.

*Primary Examiner* — Diane D Yabut

(57) ABSTRACT

A delivery system for delivering a prosthesis includes a housing, a sheath extending from within the housing, a first motor housed within the housing, a first battery coupled to the first motor, a second motor housed within the housing, a second battery coupled to the second motor, and an actuator accessible from an exterior of the housing. The actuator is coupled to the first and second batteries to selectively activate the first and second batteries to power the first and second motors, respectively. A first pulley is coupled to the first motor such that the first pulley rotates during operation of the first motor and a second pulley is coupled to the second motor such that the second pulley rotates during operation of the second motor. Actuation of the actuator causes at least one of the first and second motors to rotate, thereby causing at least one of the first and second pulleys to wind up a portion of a single continuous cable and retract the sheath.

20 Claims, 13 Drawing Sheets

(56) References Cited

U.S. PATENT DOCUMENTS

2013/0018451 A1    1/2013   Grabowski et al.
2015/0305902 A1    10/2015   Argentine
2016/0135975 A1    5/2016   Shimoyama

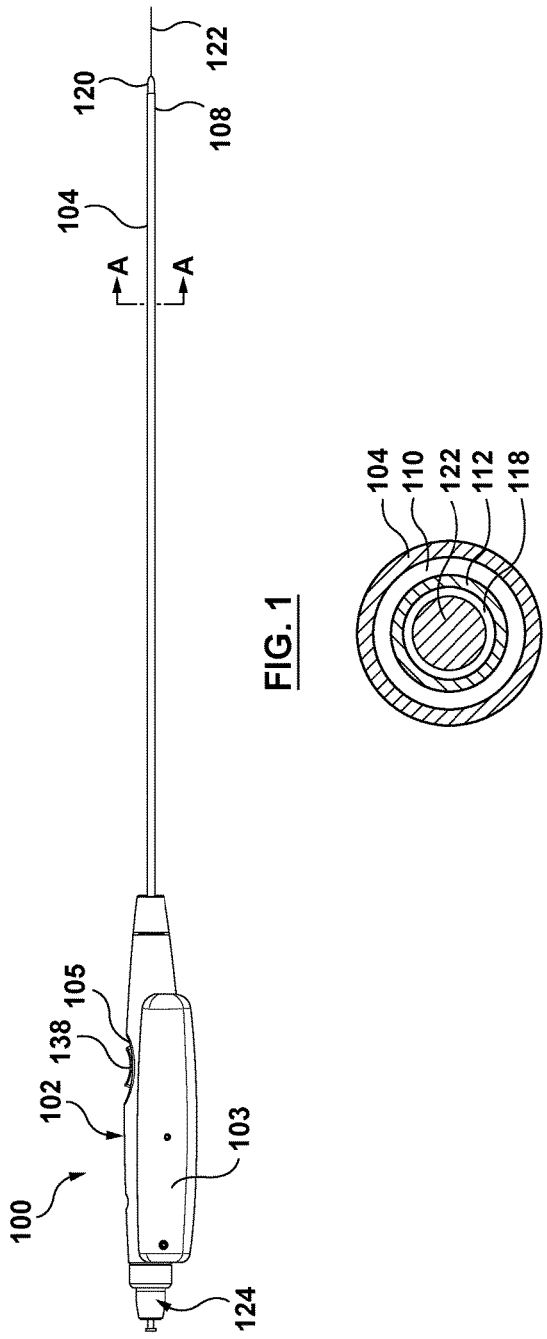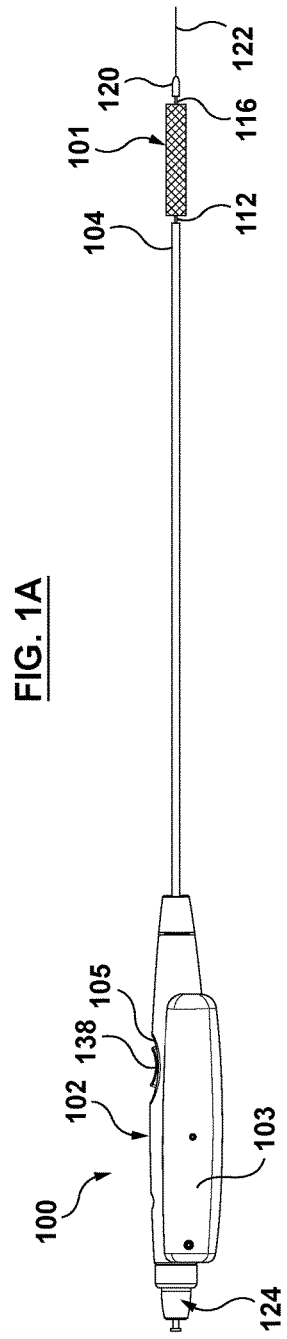

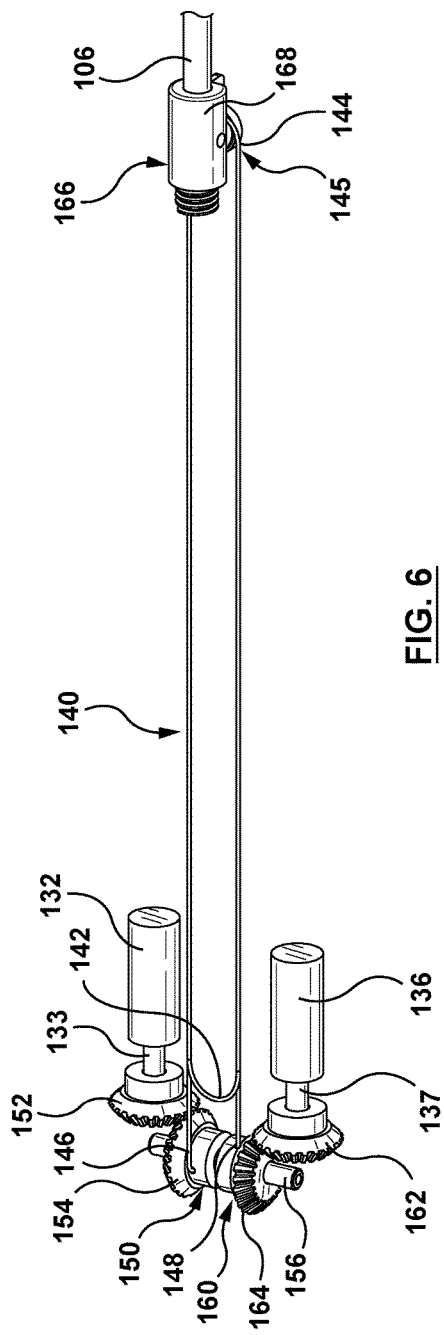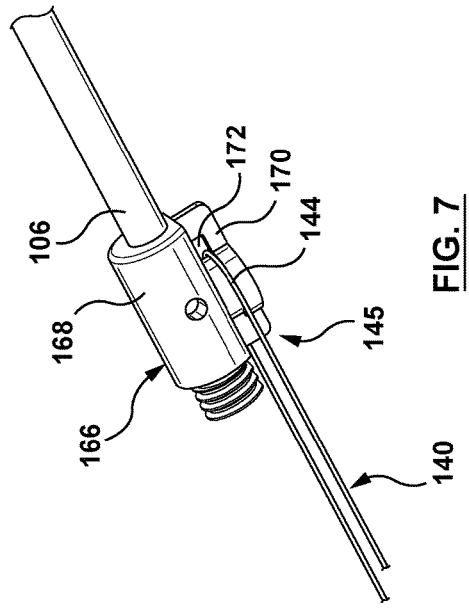

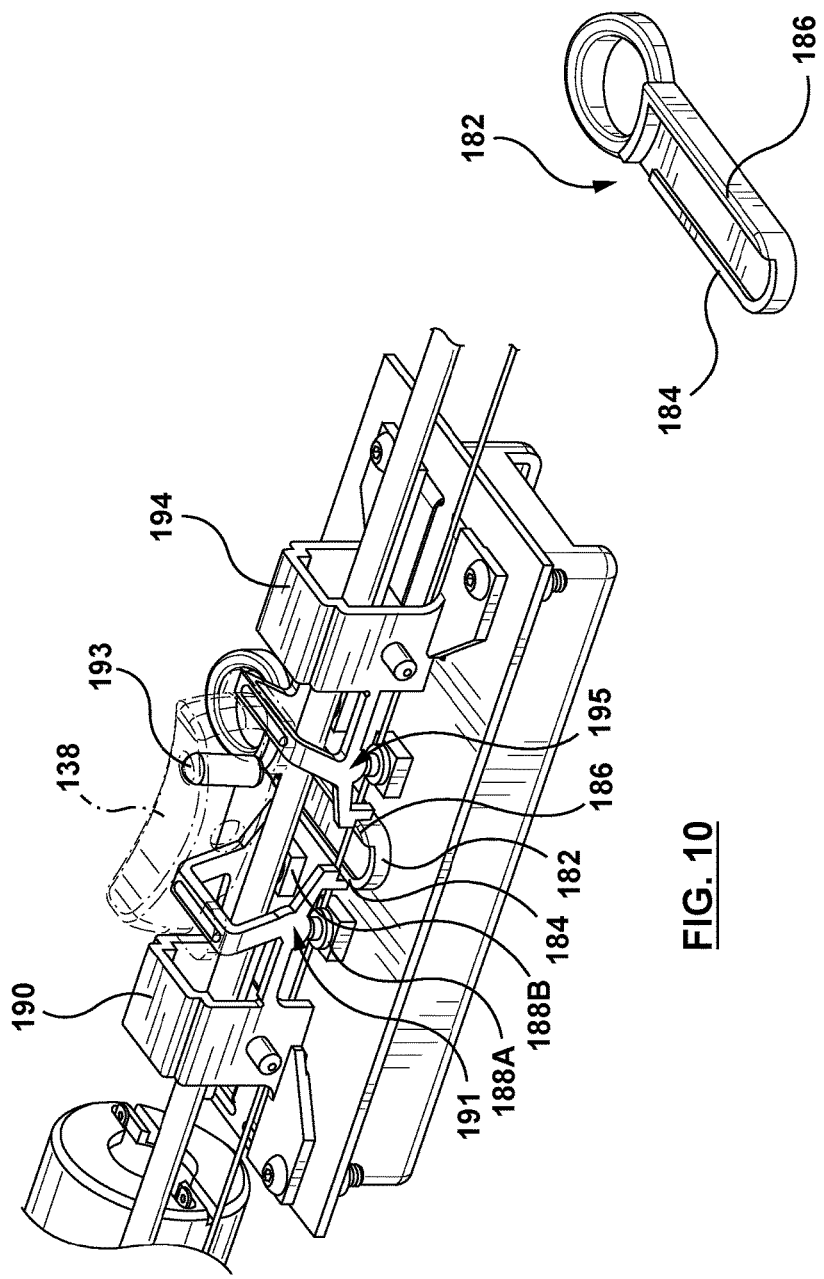

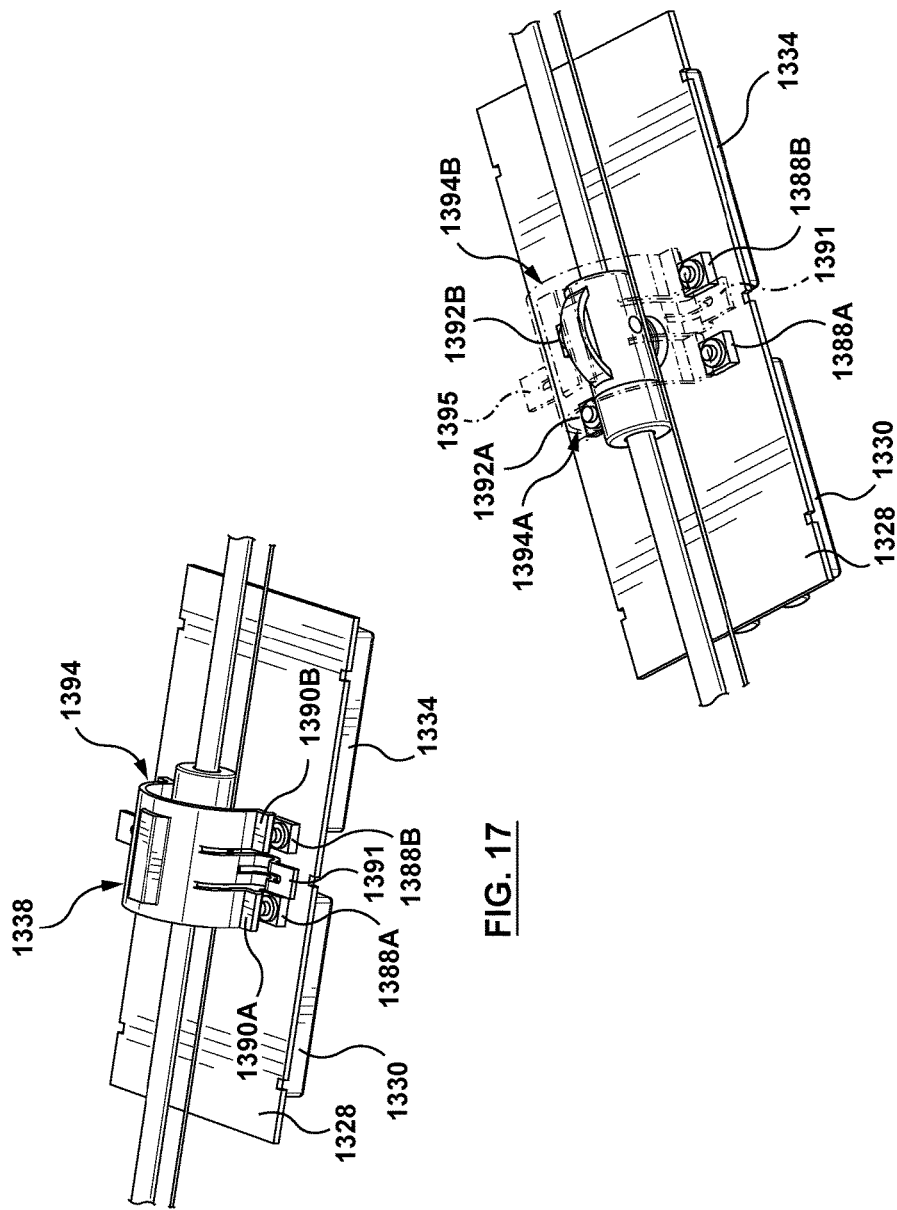

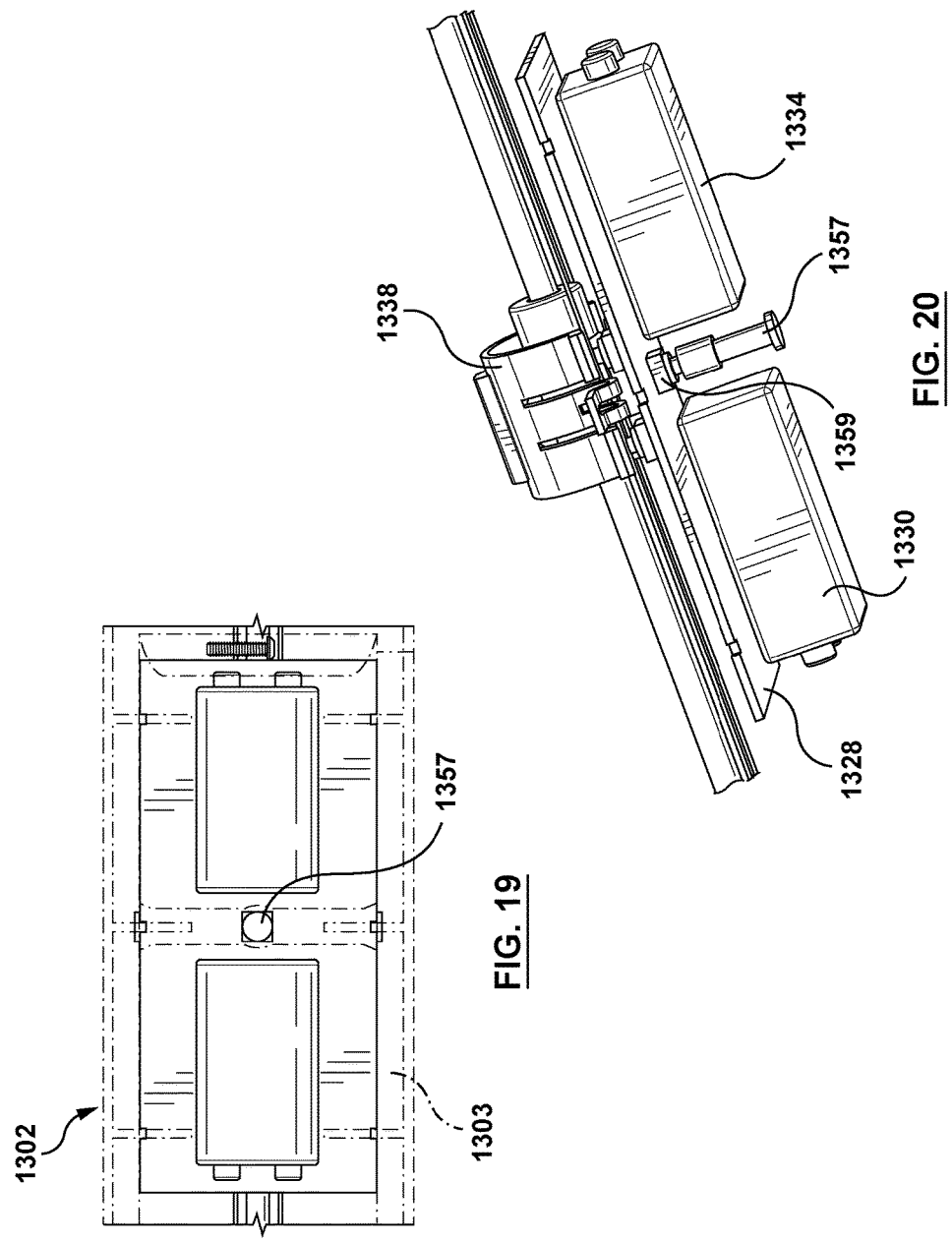

MOTORIZED DELIVERY SYSTEMS FOR AN ENOVASCULAR DEVICE

FIELD OF THE INVENTION

The invention is related in general to implantable prostheses and in particular to a delivery system configured to delivery and deploy self-expanding prostheses.

BACKGROUND OF THE INVENTION

Prostheses for implantation in blood vessels or other similar organs of the living body are, in general, well known in the medical art. For example, prosthetic vascular grafts constructed of biocompatible materials have been employed to replace or bypass damaged or occluded natural blood vessels. In general, endovascular grafts typically include a graft anchoring component that operates to hold a tubular graft component of a suitable graft material in its intended position within the blood vessel. Most commonly, the graft anchoring component is one or more radially compressible stents that are radially expanded in situ to anchor the tubular graft component to the wall of a blood vessel or anatomical conduit. Thus, endovascular grafts are typically held in place by mechanical engagement and friction due to the opposition forces provided by the radially expandable stents.

Grafting procedures are also known for treating aneurysms. Aneurysms result from weak, thinned blood vessel walls that "balloon" or expand due to aging, disease and/or blood pressure in the vessel. Consequently, aneurysmal vessels have a potential to rupture, causing internal bleeding and potentially life threatening conditions. Grafts are often used to isolate aneurysms or other blood vessel abnormalities from normal blood pressure, reducing pressure on the weakened vessel wall and reducing the chance of vessel rupture. As such, a tubular endovascular graft may be placed within the aneurysmal blood vessel to create a new flow path and an artificial flow conduit through the aneurysm, thereby reducing if not nearly eliminating the exertion of blood pressure on the aneurysm.

In general, rather than performing an open surgical procedure to implant a bypass graft that may be traumatic and invasive, endovascular grafts which may be referred to as stent-grafts are preferably deployed through a less invasive intraluminal delivery procedure. More particularly, a lumen or vasculature is accessed percutaneously at a convenient and less traumatic entry point, and the stent-graft is routed through the vasculature to the site where the prosthesis is to be deployed. Intraluminal deployment is typically effected using a delivery catheter with coaxial inner and outer tubes arranged for relative axial movement. For example, a self-expanding stent-graft may be compressed and disposed within the distal end of an outer catheter tube distal of a stop fixed to the inner member. The catheter is then maneuvered, typically routed through a body lumen until the end of the catheter and the stent-graft are positioned at the intended treatment site. The stop on the inner member is then held stationary while the outer tube of the delivery catheter is withdrawn. The stop prevents the stent-graft from being withdrawn with the sheath. As the sheath is withdrawn, the stent-graft is released from the confines of the sheath and radially self-expands so that at least a portion of it contacts and substantially conforms to a portion of the surrounding interior of the lumen, e.g., the blood vessel wall or anatomical conduit.

In recent years, to improve optimal control and alignment during deployment and positioning of a stent-graft, various tip capture spindles have been incorporated into the delivery system utilized for percutaneously delivering the stent-graft prosthesis. Tip capture involves restraining the proximal end stent of the stent-graft in a radially compressed configuration in conjunction with the main body restraint achieved by other delivery system components, such as a tubular cover shaft or sheath. The tip capture spindle can be activated at any time during stent-graft deployment to suit any number of system characteristics driven by the therapy type, stent-graft type, or specific anatomical conditions that may prescribe the release timing. Typically, the tip capture release is activated after some or all the main stent-graft body release, and thus provides a mean of restraining the stent-graft during positioning and any re-positioning. Additional restraint of the stent-graft is a key characteristic when the operator is attempting to accurately position the stent relative to an anatomical target. The tip capture restraint also aids in reducing an abrupt force of expansion when the stent-graft is released from the graft cover or sheath.

A stent-graft may be tightly compressed within a catheter for delivery, imposing high levels of friction between the stent-graft and the outer sheath of the catheter. Thus, a delivery system must be capable of imparting a significant, yet controlled, force to retract the outer sheath and deploy the stent-graft. A need in the art still exists for an improved delivery system having a handle that consistently and reliably retracts the outer sheath thereof in order to deploy a prosthesis in a body lumen.

BRIEF SUMMARY OF THE INVENTION

Embodiments hereof relate to a delivery system for delivering a prosthesis. The delivery system includes a housing, a sheath extending from within the housing, a first motor housed within the housing, a first battery coupled to the first motor for powering the first motor, the first battery housed within the housing, a second motor housed within the housing, a second battery coupled to the second motor for powering the second motor, the second battery housed within the housing, and an actuator accessible from an exterior of the housing. The actuator is coupled to the first and second batteries to selectively activate the first and second batteries to power the first and second motors, respectively. The delivery system further includes a single continuous cable having a first end coupled to a first pulley and a second end coupled to a second pulley. The first pulley is coupled to the first motor such that the first pulley rotates during operation of the first motor and the second pulley is coupled to the second motor such that the second pulley rotates during operation of the second motor. An intermediate portion of the single continuous cable is coupled to a proximal portion of the sheath and actuation of the actuator causes at least one of the first and second motors to rotate, thereby causing at least one of the first and second pulleys to wind up a portion of the single continuous cable and retract the sheath.

Embodiments hereof also relate to a delivery system that includes a housing, a sheath extending from within the housing, a first motor housed within the housing, a first battery coupled to the first motor for powering the first motor, the first battery housed within the housing, a second motor housed within the housing, a second battery coupled to the second motor for powering the second motor, the second battery housed within the housing, and an actuator accessible from an exterior of the housing. The actuator is coupled to the first and second batteries to selectively activate the first and second batteries to power the first and second motors, respectively. The delivery system further includes at least one cable coupled to a first pulley and to a second pulley, the first pulley being coupled to the first motor such that the first pulley rotates during operation of the first motor and the second pulley being coupled to the second motor such that the second pulley rotates during operation of the second motor, wherein the at least one cable is coupled to a proximal portion of the sheath and actuation of a proximal end of the actuator checks a status of the first and second batteries, and actuation of a distal end of the actuator causes both the first and second motors to rotate, thereby causing both the first and second pulleys to wind up a portion of the at least one cable and retract the sheath.

Embodiments hereof also relate to a delivery system that includes a housing, a sheath extending from within the housing, a first motor housed within the housing, a first battery coupled to the first motor for powering the first motor, the first battery housed within the housing, a second motor housed within the housing, a second battery coupled to the second motor for powering the second motor, the second battery housed within the housing, and an actuator accessible from an exterior of the housing. The actuator is coupled to the first and second batteries to selectively activate the first and second batteries to power the first and second motors, respectively. The delivery system further includes at least one cable coupled to a first pulley and to a second pulley, the first pulley being coupled to the first motor such that the first pulley rotates during operation of the first motor and the second pulley being coupled to the second motor such that the second pulley rotates during operation of the second motor, wherein the at least one cable is coupled to a proximal portion of the sheath and actuation of the actuator in a first direction causes one of the first and second motors to rotate, thereby causing one of the first and second pulleys to wind up a portion of the at least one cable and retract the sheath at a first speed, and actuation of the actuator in a second direction causes both the first and second motors to rotate, thereby causing both the first and second pulleys to wind up a portion of the at least one cable and retract the sheath at a second speed, the second speed being faster than the first speed.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side view of a delivery system according to an embodiment hereof, wherein an outer sheath of the delivery system surrounds and constrains a prosthesis in a compressed or delivery configuration.

FIG. 1A is a cross-sectional view taken along line A-A of FIG. 1.

FIG. 2 is a side view of the delivery system of FIG. 1, wherein the outer sheath has been retracted via a handle of the delivery system in order to allow the prosthesis to self-expand to a deployed or expanded configuration.

FIG. 6 is a perspective view of select components of the handle of the delivery system of FIG. 1 to illustrate a single continuous cable of the handle of the delivery system of FIG. 1, wherein the other components of the handle have been removed for illustrative purposes.

FIG. 7 is an enlarged perspective view of a portion of FIG. 6, wherein the single continuous cable is shown looped through an anchor.

FIG. 10 is a perspective enlarged view of the actuator (shown in phantom) and the first and second batteries of the handle of the delivery system of FIG. 1, wherein the housing of the handle has been removed for illustrative purposes.

FIG. 11 is a perspective view of a removable tab of the handle of the delivery system of FIG. 1, wherein the removable tab has been removed from the handle for illustrative purposes.

FIG. 17 is a perspective enlarged view of an actuator and the first and second batteries of the handle of the delivery system of FIG. 13, wherein the housing of the handle has been removed for illustrative purposes.

FIG. 18 is a perspective enlarged view of the actuator (shown in phantom) and the first and second batteries of the handle of the delivery system of FIG. 13, wherein the housing of the handle has been removed for illustrative purposes.

FIG. 19 is a bottom view of a second actuator and the first and second batteries of the handle of the delivery system of FIG. 13, wherein the housing of the handle is shown in phantom for illustrative purposes.

FIG. 20 is a perspective exploded view of the second actuator and the first and second batteries of the handle of the delivery system of FIG. 13, wherein the housing of the handle is removed for illustrative purposes.

DETAILED DESCRIPTION OF THE INVENTION

Figure 3:
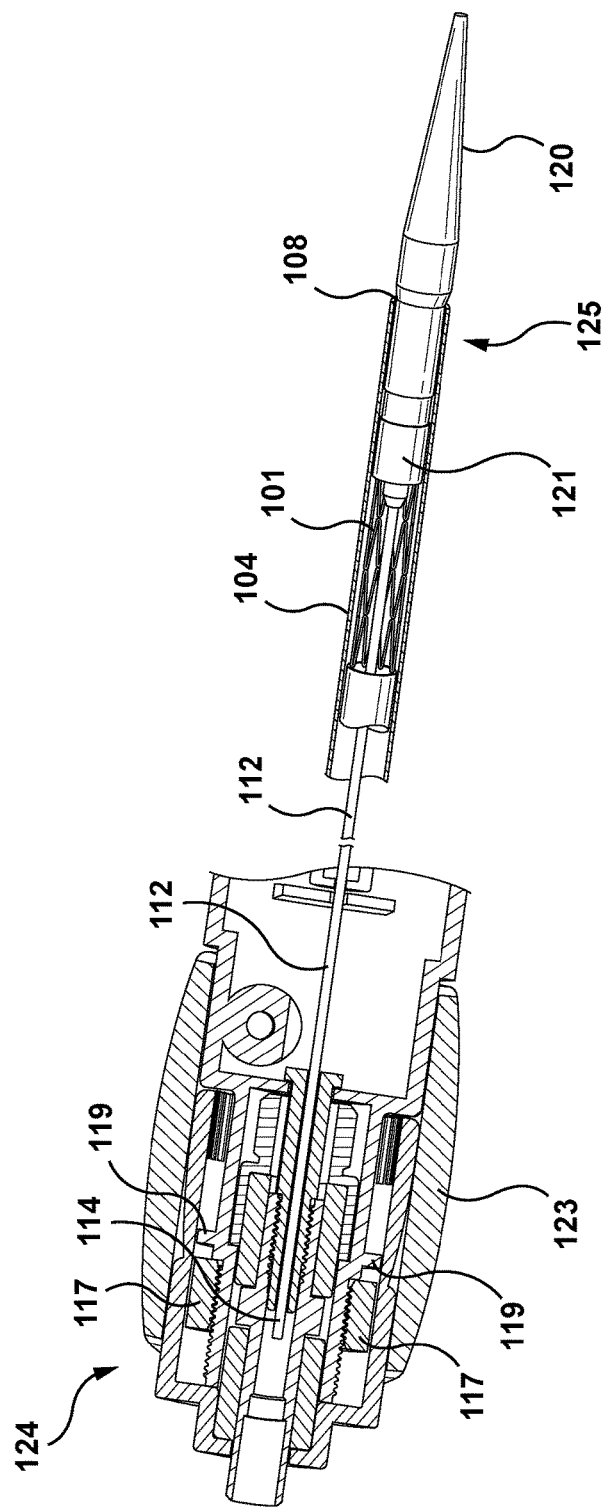
FIG. 3 depicts a sectional view of a tip release mechanism of the handle of the delivery system of FIG. 1 and a tip capture device of the delivery system of FIG. 1.

Specific embodiments of the present invention are now described with reference to the figures, wherein like reference numbers indicate identical or functionally similar elements. Specific embodiments are now described with reference to the figures, wherein like reference numbers indicate identical or functionally similar elements. Unless otherwise indicated, for the delivery system the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. For the stent-graft prosthesis "proximal" is the portion nearer the heart by way of blood flow path while "distal" is the portion of the stent-graft further from the heart by way of blood flow path. In addition, the term "self-expanding" is used in the following description with reference to one or more stent structures of the prostheses hereof and is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

The following detailed description is merely exemplary in nature and is not intended to limit the invention or the application and uses of the invention. Although the description of the invention is in the context of treatment of blood vessels such as the aorta, coronary, carotid and renal arteries, the invention may also be used in any other body passageways where it is deemed useful. Furthermore, there is no intention to be bound by any expressed or implied theory presented in the preceding technical field, background, brief summary or the following detailed description.

Embodiments hereof are related to a delivery system having an improved handle that maintains accuracy in delivery and deployment of a prosthesis in a body lumen. With reference to FIGS. 1, 1A, and 2, a delivery system 100 includes a handle 102 having a housing 103, an inner shaft 112 having a proximal end 114 (shown on FIG. 3) and a distal end 116, and an outer retractable sheath or cover 104 having a proximal end 106 (shown on FIGS. 6 and 7) and a distal end 108. Both outer sheath 104 and inner shaft 112 extend from within housing 103 of handle 102. FIG. 1 is a side view of delivery system 100, with outer sheath 104 shown in a delivery configuration in which outer sheath 104 surrounds and constrains a prosthesis 101 in a compressed or delivery configuration. FIG. 1A is a cross-sectional view taken along line A-A of FIG. 1. FIG. 2 is a side view of delivery system 100 after outer sheath 104 has been retracted via handle 102 in order to allow prosthesis 101 to self-expand to a deployed or expanded configuration. Handle 102 includes a tip capture mechanism 124, which will be explained in more detail herein with respect to FIG. 3, and a sheath retraction mechanism 105 for retracting outer sheath 104 as will be explained in more detail herein with respect to FIGS. 4-12. As best shown in FIG. 1A, outer sheath 104 defines a lumen 110 and outer sheath 104 is slidingly disposed over inner shaft 112. Inner shaft 112 defines a lumen 118 such that delivery system 100 may be slidingly disposed and track over a guidewire 122. A tapered flexible nosecone or tip 120 may be coupled to distal end 116 of inner shaft 112. Prosthesis 101 is mounted over inner shaft 112 at a distal portion thereof and outer sheath 104 surrounds and constrains prosthesis 101 in a compressed or delivery configuration as shown in the side view of FIG. 1 (prosthesis 101 shown only in the view of FIG. 2). Proximal end 106 of outer sheath 104 is operably coupled to sheath retraction mechanism 105 of handle 102. During deployment of prosthesis 101, sheath retraction mechanism 105 is operated via an actuator 138 accessible from an exterior of housing 103 in order to proximally retract outer sheath 104 to thereby incrementally expose prosthesis 101. Once prosthesis 101 is properly positioned, outer sheath 104 is retracted to fully expose prosthesis 101 and thereby permit full release of prosthesis 101 from delivery system 100, as explained in more detail below. The deployed configuration of prosthesis 101 is merely exemplary, and it would be apparent to one of ordinary skill in the art that delivery system 100 may be utilized for delivering and deploying various types or configurations of self-expanding prostheses.

According to an embodiment hereof, handle 102 also includes a flush shaft or lumen 126 having a port 127 that is accessible from an exterior of housing 103 of handle 102. Flush shaft 126 is concentrically disposed over a proximal portion of inner shaft 112, and the lumen of flush shaft 126 is in fluid communication with lumen 110 of outer sheath 104. Flush shaft 126 may be utilized to flush out or eliminate air in the delivery system and/or prosthesis 101 to prevent such air from being released into the blood stream as will be understood by one of ordinary skill in the art.

FIG. 3 depicts a sectional view of tip release mechanism 124 of handle 102 attached to proximal end 114 of inner shaft 112 and a tip capture device 125 of delivery system 100 that is attached to distal end 116 of inner shaft 112. For ease of illustration a remainder of delivery system 100 is removed from FIG. 3 with a portion of prosthesis 101 being shown in a compressed, delivery configuration within a distal portion of outer sheath 104. Tip capture mechanism 124 is described in more detail in U.S. Pat. No. 9,486,350 to Argentine, which is hereby incorporated by reference herein in its entirety. In a delivery configuration, distal end 108 of outer sheath 104 abuts with tip capture device 125, such that together outer sheath 104 and tip capture device 125 hold a stent-graft in a compressed delivery configuration within a distal portion of delivery system 101. A proximal end of prosthesis 101 is held within a distal sleeve 121 and a spindle (not shown in FIG. 3) of tip capture device 125. Tip release mechanism 124 is operably coupled to tip capture device 125 such that rotation of inner shaft 112 in a first direction moves or distally advances distal sleeve 121 relative to the spindle and a proximal end of prosthesis 101 is released in two distinct steps or stages, wherein during a first step or stage the proximal end of prosthesis 101 is partially uncovered and during a second step or stage the proximal end of prosthesis 101 is fully uncovered and released from tip capture device 125. Tip release mechanism 124 includes a rotatable grip component 123 that is operably coupled to proximal end 114 of inner shaft 112. As more fully described in U.S. Pat. No. 9,486,350 to Argentine, previously incorporated by reference, rotation of grip component 123 in each of a first and second direction rotates the inner shaft 112 in the first direction, which causes distal advancement of distal sleeve 121 of tip capture device 125 to provide the two-stage release of the proximal end of prosthesis 101. Rotation of grip component 123 in the first direction concurrently longitudinally translates a stop component 117 in a distal direction until stop component 117 contacts a hard stop 119 of housing 103 of handle 102. The contact of stop component 117 with hard stop 119 prevents further rotation of the grip component 123 in the first direction, as stop component 117 can no longer move in the distal direction. Thereafter rotation of grip component 123 may continue only in the second direction, which longitudinally translates stop component 117 in a proximal direction while maintaining rotation of inner shaft 112 in the first direction to thereby continue the distal advancement of distal sleeve 121.

In operation, when prosthesis 101 held in a delivery configuration by delivery system 101 is to be deployed, sheath retraction mechanism 105 is operated to retract outer sheath 104 in a proximal direction such that distal end 108 no longer covers or extends over the proximal end of prosthesis 101. Grip component 123 is then rotated in the first direction to perform the first step or stage of tip release described above. The first stage of tip release has been performed when grip component 123 can no longer be rotated in the first direction, wherein distal sleeve 121 of tip capture device 125 will have been distally advanced a sufficient distance to partially uncover the proximal end of prosthesis 101, which permits prosthesis 101 to transition from a delivery state to a partially deployed state. With the proximal end of prosthesis 101 in the partially deployed state, a clinician via fluoroscopy may assure proper positioning at a treatment site of the proximal end of prosthesis 101 before full deployment of prosthesis 101. Accordingly, if the proximal end of prosthesis 101 is found to be not properly positioned at this stage of the procedure, the clinician may "push" or otherwise manipulate the proximal end of prosthesis 101 until proper placement is confirmed. Thereafter sheath retraction mechanism 105 is operated to continue proximal retraction of outer sheath 104 until the remaining length of prosthesis 101 is completely uncovered, and thus allowed to release or deploy from delivery system 101. At this point of operation, prosthesis 101 is no longer covered by outer sheath 104 but the proximal end of prosthesis 101 is still coupled to tip capture device 125. Grip component 123 is then rotated in the second direction to perform the second step or stage of tip release described above. Once distal sleeve 121 of tip capture device 125 is distal of the proximal end of prosthesis 101, the second stage of tip release has been performed, wherein the proximal end of prosthesis 101 release from or move free of tip capture device 125 and the proximal end of prosthesis 101 transitions from the partially deployed state to a fully deployed state. With the release of the proximal end of prosthesis 101 from tip capture device 125, prosthesis 101 is fully deployed.

Figure 4:
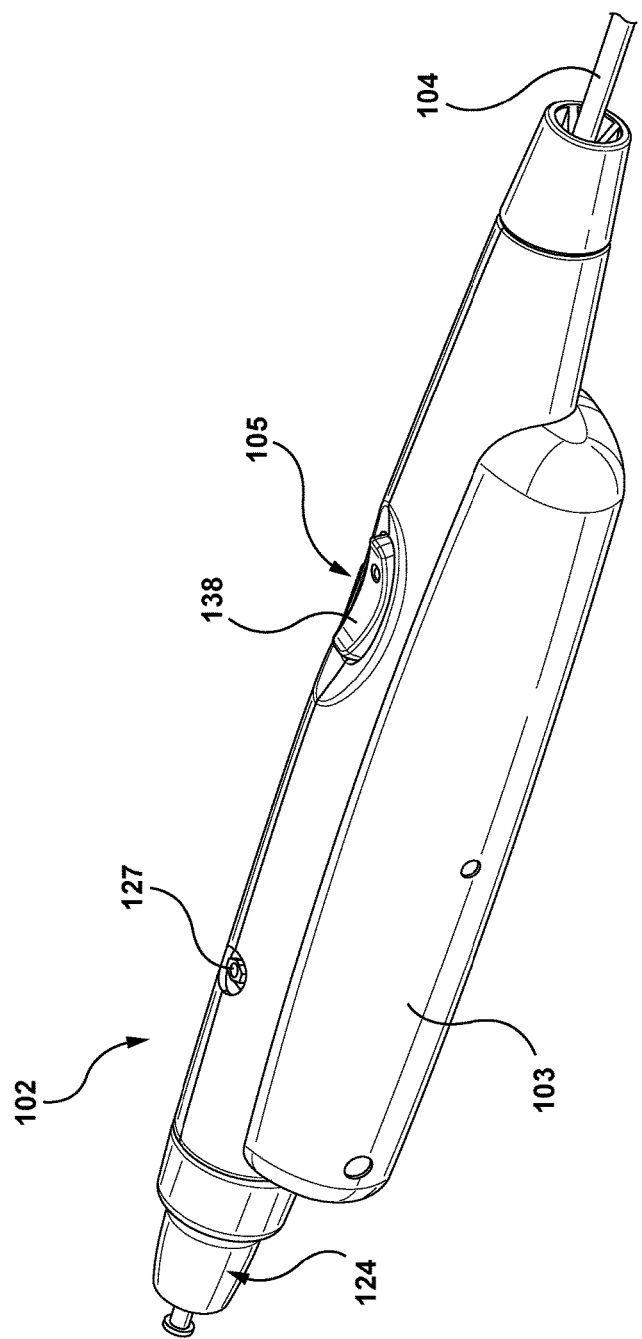
FIG. 4 is a perspective enlarged view of the handle of the delivery system of FIG. 1.
Figure 5:
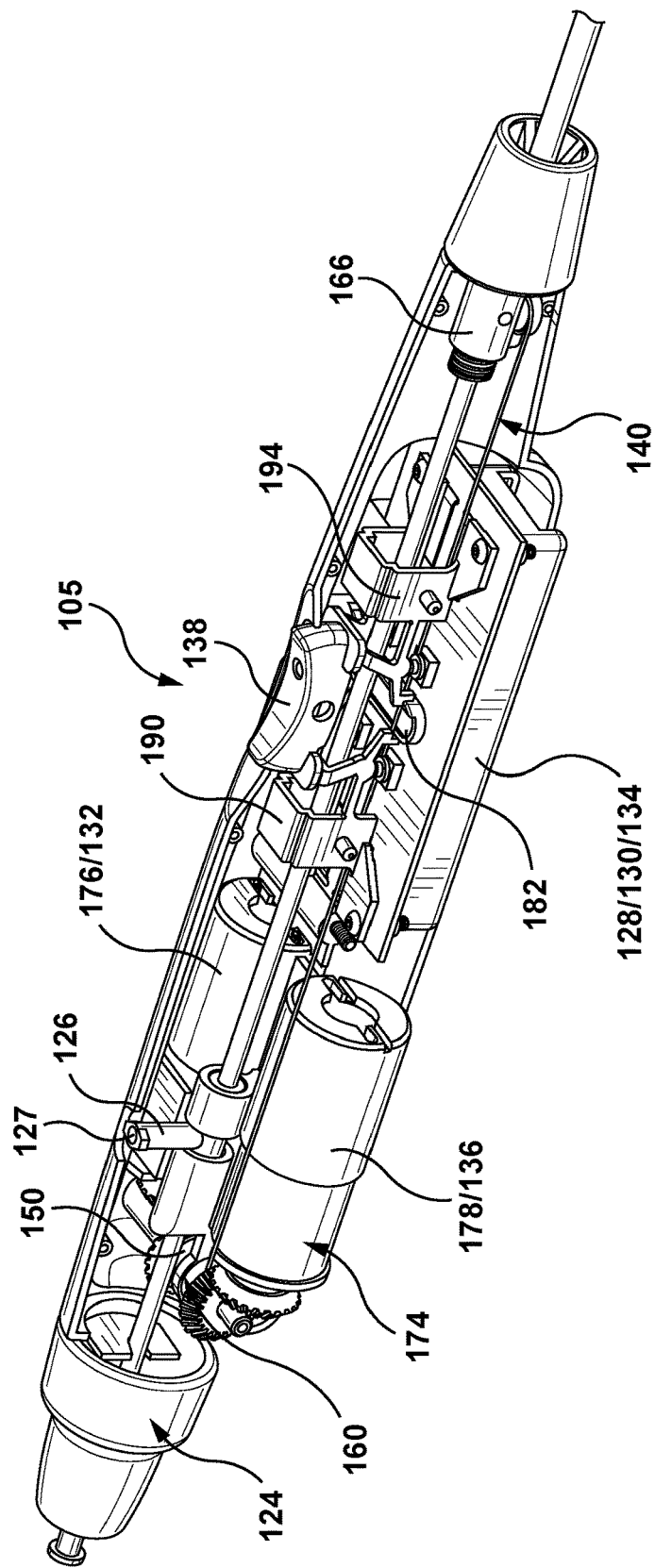
FIG. 5 is a perspective enlarged view of the handle of the delivery system of FIG. 1, wherein a portion of a housing of the handle has been removed for illustrative purposes.

Sheath retraction mechanism 105 for retracting outer sheath 104 will now be described in more detail with respect to FIGS. 4-12. FIGS. 4 and 5 are perspective enlarged views of handle 102, with a portion of housing 103 removed in FIG. 5 to illustrate the internal components of handle 102. As will be explained in more detail herein, sheath retraction mechanism 105 includes a first motor 132 housed within housing 103 of handle 102 and a second motor 136 housed within housing 103 of handle 102 for retracting outer sheath 104. First and second motors 132, 136 are selectively collectively or simultaneously actuated for proximally retracting outer sheath 104 in order to deploy or release prosthesis 101, thereby allowing prosthesis 101 to self-expand to a deployed or expanded configuration as shown in the side view of FIG. 2. Stated another way, a user operates handle 102 of delivery system 100 in order to withdraw or proximally retract outer sheath 104, thereby releasing prosthesis 101 at a desired location in a patient's body lumen. In addition to first and second motors 132, 136, housing 103 of handle 102 also houses a first battery 130 coupled to first motor 132 for powering the first motor and a second battery 134 coupled to second motor 136 for powering the second motor. Actuator 138 is operatively coupled to first and second batteries 130, 134 to selectively collectively or simultaneously activate the first and second batteries to power first and second motors 132, 136, respectively. As described in more detail herein, in this embodiment first and second motors 132, 136 are configured to be operated in tandem, or simultaneously, in order to retract outer sheath 104 at a relatively quicker or faster rate as compared to manual retraction and/or retraction with only a single motor. However, if one of first and second motors 132, 136 (or one of first and second batteries 130, 134, respectively) fail to operate, sheath retraction mechanism 105 is configured to retract outer sheath 104 with only one operating motor (i.e., the other of first and second motors 132, 136). Stated another way, sheath retraction mechanism 105 still operates to retract outer sheath 104 if one of first and second motors 132, 136 malfunctions or if one of first and second batteries 130, 134 does not have sufficient charge to power its respective motor.

FIG. 6 is a perspective view of select components of handle 102 to illustrate operation of first and second motors 132, 136 with single continuous cable 140. Housing 103 and various other components of the handle have been removed to isolate components described in relation to FIG. 6. In addition to first and second motors 132, 136 and their respective first and second batteries 130, 134, sheath retraction mechanism 105 further includes a single continuous cable 140 having a first end 146 coupled to a first pulley 150, a second end 148 coupled to a second pulley 160, and an intermediate portion 145 coupled to proximal end 106 of outer sheath 104. Each of first and second pulleys 150, 160 include a circumferential groove or channel formed on an outer surface thereof for receiving cable 140. Single continuous cable 140 may be formed from any sufficiently strong suitable material, including but not limited to Kevlar® or other suitable synthetic fiber.

First pulley 150 is coupled to first motor 132 via bevel gears 152, 154 such that first pulley 150 rotates during operation of first motor 132. More particularly, gear 152 is attached to or mounted over a motor shaft 133 of first motor 132 and rotates therewith. Gear 154 is attached to or mounted over a joint shaft 156 that extends between first pulley 150 and second pulley 160 and rotates therewith. First pulley 150 is also attached to or mounted over joint shaft 156 that extends between first pulley 150 and second pulley 160 and rotates therewith. Motor shaft 133 and joint shaft 156 are disposed 90° apart, and bevel gears 152, 154 function to transfer the rotational force of first motor 132 to first pulley 150. Similarly, second pulley 160 is coupled to second motor 136 such that second pulley 160 rotates during operation of second motor 136. Gear 162 is attached to or mounted over a motor shaft 137 of second motor 136 and rotates therewith. Gear 164 is attached to or mounted over joint shaft 156 that extends between first pulley 150 and second pulley 160 and rotates therewith. Second pulley 160 is also attached to or mounted over joint shaft 156 that extends between first pulley 150 and second pulley 160 and rotates therewith. Motor shaft 137 and joint shaft 156 are disposed 90° apart, and bevel gears 162, 164 function to transfer the rotational force of second motor 136 to second pulley 160.

First and second motors 132, 136 are configured to rotate in opposing directions in order to simultaneously rotate joint shaft 156 in the same direction (i.e., clockwise or counter-clockwise). For example, first motor 132 rotates in a first or clockwise direction and second motor 136 rotates in a second or counter-clockwise direction. In another example, first motor 132 rotates in a counter-clockwise direction and second motor 136 rotates in a clockwise direction. Since joint shaft 156 that extends between first pulley 150 and second pulley 160 and rotates therewith, joint shaft 156 may be considered a gear axle and gears 164, 154 attached thereto may be considered a joined gear. Joint shaft 156, first pulley 150, and second pulley 160 are collectively driven by first and/or second motors 132, 136 and rotate simultaneously in the same direction. Stated another way, due to joint shaft 156, first and second pulleys 150, 160 are configured to be rotated simultaneously with rotation of either first or second motor 132, 136.

As will be described in more detail herein, actuation of actuator 138 causes at least one of first and second motors 132, 136 to rotate. When at least one of first and second motors 132, 136 rotates, both first and second pulleys 150, 160 also rotate via joint shaft 156. When first and second pulleys 150, 160 rotate, a portion of single continuous cable 140 winds around each of first and second pulleys 150, 160 and outer sheath 104 is proximally retracted. Stated another way, with first end 146 of cable 140 fixed or attached to first pulley 150 and second end 148 of cable 140 fixed or attached to second pulley 160, cable 140 wraps or circles around each of first pulley 150 and second pulley 160 when joint shaft 156, first pulley 150, and second pulley 160 are collectively driven by first and/or second motors 132, 136. If only one of first and second motors 132, 136 rotates, single continuous cable 140 winds around each of first and second pulleys 150, 160 and outer sheath 104 is proximally retracted at a first rate or speed. If both of first and second motors 132, 136 rotate, single continuous cable 140 winds around each of first and second pulleys 150, 160 and outer sheath 104 is proximally retracted at a second rate or speed that is twice as fast as the first rate or speed. Thus, if both first and second motors 132, 136 are functioning properly, outer sheath 104 is proximally retracted very quickly, i.e., at a rate of 0.50 inches per second. Conversely, if only one of first and second motors 132, 136 is functioning properly, outer sheath 104 is still proximally retracted quickly, i.e., at a rate of 0.25 inches per second and sheath retraction mechanism 105 operates despite one motor or battery malfunctioning. However, as will be understood by one of ordinary skill in the art, the time required for full retraction of outer sheath 104 may vary depending upon the length of prosthesis 101, the distance that outer sheath 104 is required to travel in order to fully release the prosthesis, whether both motors and batteries are operating and how much of cable 140 is wound per rotation of the pulleys. As also will be understood by one of ordinary skill in the art, the length of cable 140 wound with each rotation of the pulleys may be varied by changing the size of first and second pulleys 150, 160. For example, in an embodiment, the size/diameter of at least second pulley 160 may be increased in order to increase the rate at which outer sheath 104 is proximally retracted when both first and second motors 132, 136 are operating.

As cable 140 is wound or circled around first and second pulleys 150, 160, outer sheath 104 moves proximally and axially with respect to housing 103 of housing 102. Continued operation of first and/or second motors 132, 136 results in continued winding of cable 140 until outer sheath 104 is sufficiently proximally retracted to release prosthesis 101. In an embodiment hereof, a limit switch (not shown) may be utilized to indicate that prosthesis 101 is fully exposed or released from outer sheath 104. When prosthesis 101 is fully exposed or released from outer sheath 104, the limit switch causes first and second motors 132, 136 to stop and therefore limits the axial movement of outer sheath 104 with respect to housing 102. In another embodiment, a stopper (not shown), may be mounted over inner shaft 112 to limit the axial movement of outer sheath 104 with respect to housing 102. When deploying prosthesis 101, outer sheath 104 is proximally retracted until its proximal end 106 abuts against or contacts the stopper. At the point in which outer sheath 104 abuts against the stopper, prosthesis 101 is fully exposed or released from outer sheath 104 and permitted to self-expand to the deployed configuration as shown in FIG. 2.

As best shown in FIG. 7, intermediate portion 145 of single continuous cable 140 is coupled to proximal end 106 of outer sheath 104 via an anchor 166. Anchor 166 includes an annular portion 168 which surrounds and attaches to or is mounted over proximal end 106 of outer sheath 104. Anchor 166 further includes a stem or tab 170 that extends from annular portion 168 and includes a channel or passageway 172 formed therethrough. Intermediate portion 145 of single continuous cable 140 includes a distal loop 144 that extends through passageway 172 of anchor 166 in order to couple the intermediate portion of the single continuous cable to proximal end 106 of outer sheath 104. An advantage of utilizing single continuous cable 140 with first and second pulleys 150, 160 rather than two pulleys that each have a separate cable attached thereto for retracting outer sheath 104 is that single continuous cable 140 is balanced between first and second motors 132, 136. As such, each motor can contribute an equal amount of force to retract outer sheath 104 and each motor thus operates efficiently. Conversely, in a system having two pulleys that each have a separate cable attached thereto for retracting outer sheath 104, the two separate cords have a tendency to become unbalanced and one of the motors contributes most of or all the force required to retract outer sheath 104. In addition, utilizing a single continuous cable that winds around both first and second pulleys 150, 160 via at least one integral loop (i.e., distal loop 144) rather than two separate cables (i.e., a separate cable for each pulley) provides a mechanical advantage that amplifies the force applied for retracting outer sheath 104. More particularly, when only one of first and second motors 132, 136 are operating, the force output by a single continuous cable that winds around both first and second pulleys 150, 160 may be twice as much as a force output by a system that uses two separate cables. Stated another way, single continuous cable 140 having at least one integral loop (i.e., distal loop 144) provides twice the force for retracting outer sheath 104 at half the speed.

Figure 8:
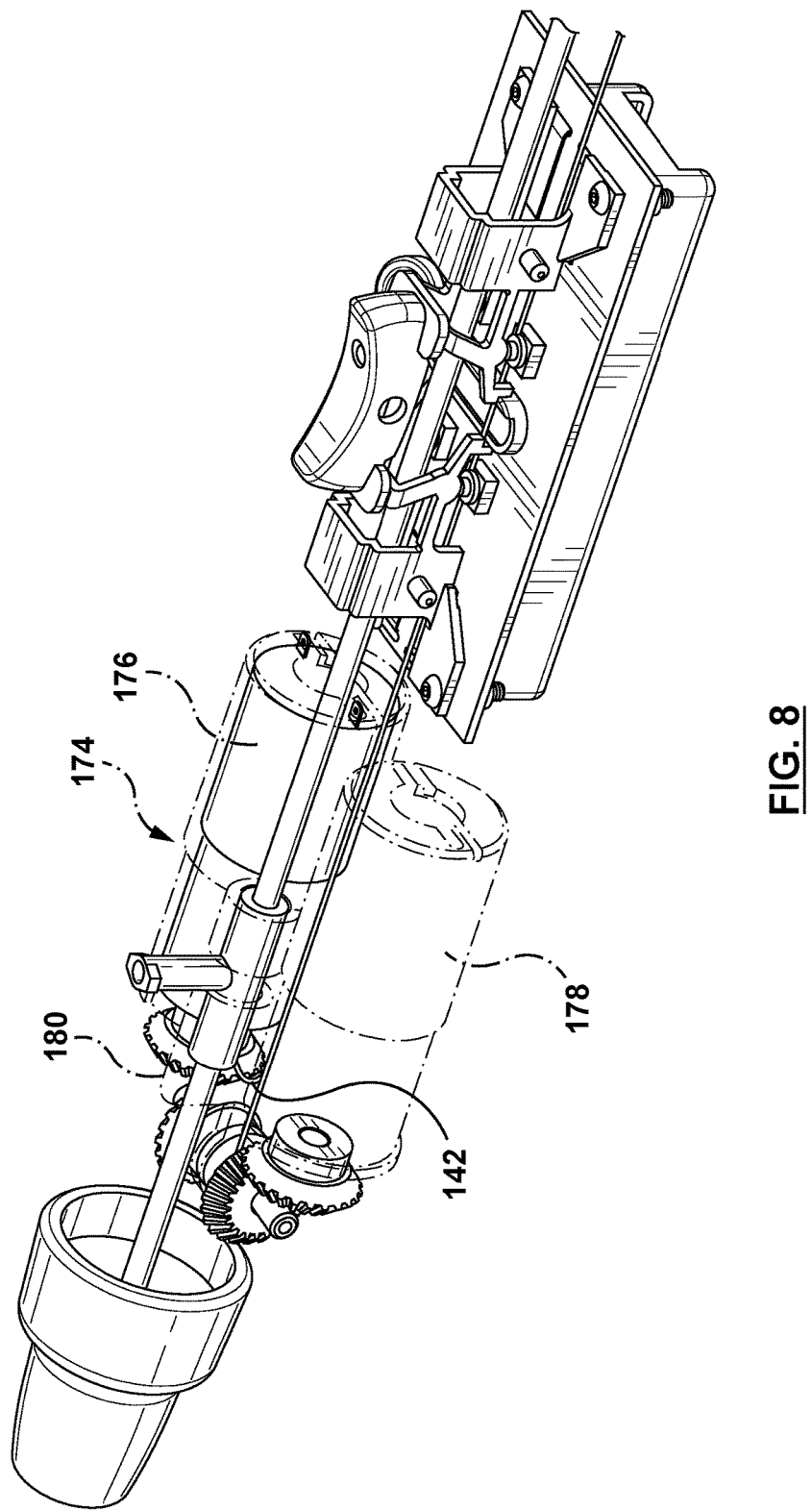
FIG. 8 is a perspective enlarged view of the handle of the delivery system of FIG. 1, wherein the housing of the handle has been removed for illustrative purposes and components thereof are shown in phantom to illustrate placement of the single continuous cable of the handle of the delivery system of FIG. 1.

Notably, in the embodiment depicted in FIG. 7, single continuous cable 140 also includes a second intermediate portion having a proximal loop 142 that extends around a portion of a mount 174 that holds first and second motors 132, 136. More particularly, FIG. 8 is a perspective enlarged view of handle 102 with housing 103 removed for illustrative purposes and mount 174 is shown in phantom to illustrate placement of single continuous cable 140. Mount 174 includes a first tubular portion 176 for receiving first motor 132, a second tubular portion 178 for receiving second motor 136, and a connector 180 extending between first and second tubular portions 176, 178. Proximal loop 142 extends around an outer surface of connector 180 of mount 174. As such, single continuous cable 140 is an elongated element with first end 146 coupled to first pulley 150, second end 148 coupled to second pulley 160, and the length of single continuous cable 140 is looped around anchor 166 and connector 180 of mount 174. Having both proximal loop 142 and distal loop 144 further increases the mechanical advantage provided by single continuous cable 140 described above with respect to distal loop 144. However, proximal loop 142 is not required and sheath retraction mechanism 105 provides a mechanical advantage with only one integral loop (i.e., distal loop 144).

Figure 9:
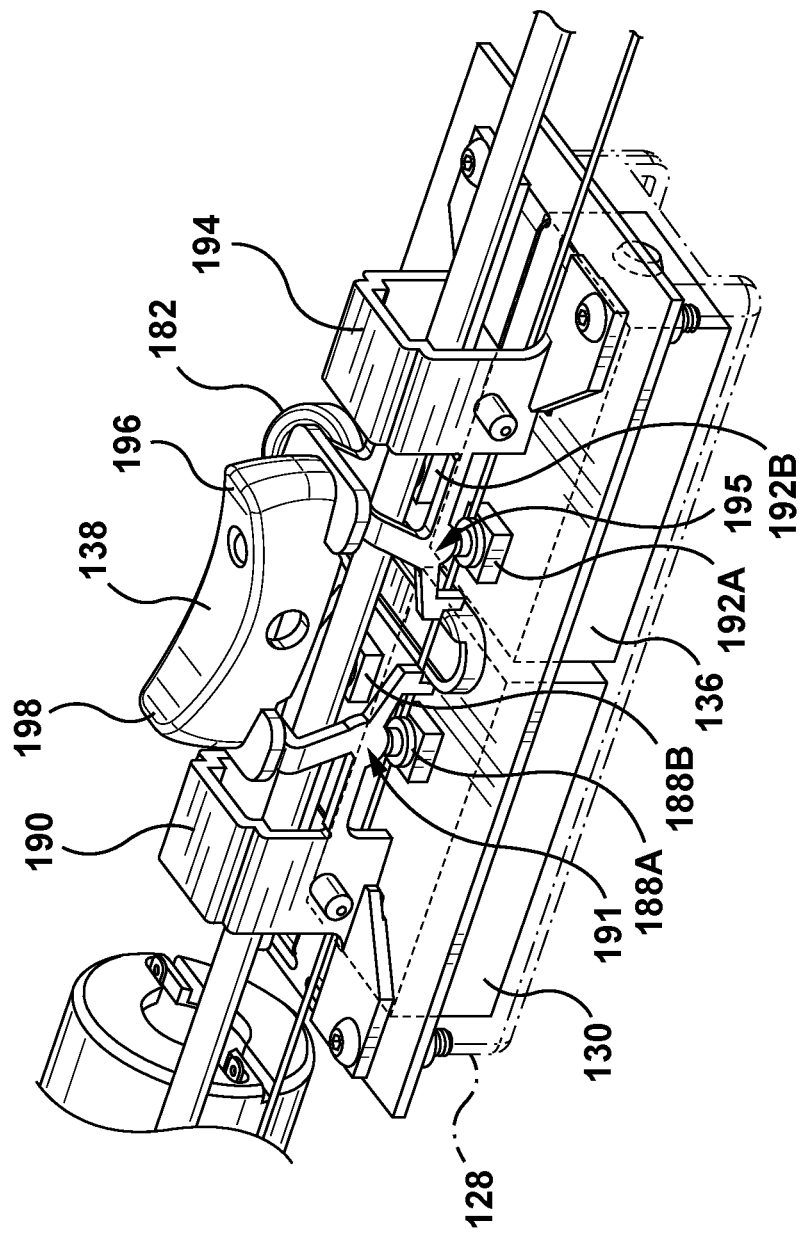
FIG. 9 is a perspective enlarged view of an actuator and the first and second batteries of the handle of the delivery system of FIG. 1, wherein the housing of the handle has been removed for illustrative purposes.

Actuation of actuator 138, which causes at least one of first and second motors 132, 136 to rotate, will now be described in more detail with reference to FIGS. 9-12. FIG. 9 is a perspective enlarged view of actuator 138 and first and second batteries 130, 134, and housing 103 of handle 102 has been removed for illustrative purposes. Actuator 138 is a rocker switch in which a first or proximal end 198 thereof is configured to be tilted or moved in a first or downward direction and a second or distal end 196 thereof is also configured to be tilted or moved in the first or downward direction. Handle 102 also includes a first or proximal connector 190, a second or distal connector 194, first and second switches 188A, 188B, third and fourth switches 192A, 192B, and an indicator light 193. First and second batteries 130, 134 are housed within a battery housing 128 (shown in phantom in FIG. 9). One outer surface or wall of battery housing 128 is formed by or includes a printed circuit board. First and second switches 188A, 188B and third and fourth switches 192A, 192B are all electrically coupled to first and second batteries 130, 134 as will be described in more detail herein. Proximal connector 190 is fixed or attached to an outer surface of battery housing 128, and a lever portion 191 thereof is movable with respect to battery housing 128. Similarly, distal connector 194 is fixed or attached to an outer surface of battery housing 128, and a lever portion 195 thereof is movable with respect to battery housing 128. Lever portion 191 of proximal connector 190 is axially aligned with proximal end 198 of rocker switch 138, while lever portion 195 of distal connector 194 is axially aligned with distal end 196 of rocker switch 138. When proximal end 198 of actuator or rocker switch 138 is actuated in the first direction such that proximal end 198 is depressed or moved in a downward direction, a status check of first and second batteries 130, 134 is performed but neither first and second motors 132, 136 rotate. When distal end 196 of actuator or rocker switch 138 is actuated such that distal end 196 is depressed or moved in a downward direction, first and second motors 132, 136 simultaneously rotate (assuming batteries 130, 136 and motors 132, 136 are all functioning properly), thereby causing both first and second pulleys 150, 160 to wind up single continuous cable 140 and retract outer sheath 104 as described above.

Handle 102 includes a removable tab 182, which is shown removed from handle 102 in FIG. 11 and is shown slidingly disposed within handle 102 in FIGS. 9 and 10. Removable tab 182 includes a first or proximal edge 184 and a second or distal edge 186. Removable tab 182 is a generally planar or flat component except that distal edge 186 is raised or elevated relative to the rest of the planar component. Distal edge 186 may be considered a ridge of removable tab 182 that extends around a portion of a perimeter of removable tab 182. When removable tab 182 is slidingly disposed within housing 102 as shown in FIGS. 9 and 10, proximal edge 184 is adjacent to lever portion 191 of proximal connector 190 and raised distal edge 186 is adjacent to lever portion 195 of distal connector 194. Removable tab 182 is disposed within handle 102 until such time that delivery system 100 is to be operated.

The status check function of actuator 138 will be described in more detail with reference to FIG. 10. When proximal end 198 of actuator or rocker switch 138 is actuated in the first direction such that proximal end 198 is depressed or moved in a downward direction, proximal end 198 of rocker switch 138 moves or depresses lever portion 191 of proximal connector 190 such that lever portion 191 contacts and activates first and second switches 188A, 188B. First and second switches 188A, 188B are electrically coupled to first and second batteries 130, 134 such that when activated a status check of first and second batteries 130, 134 is performed but neither first and second motors 132, 136 rotate. For example, circuitry on the printed circuitry board of battery housing 128 will interrogate the status of first and second motors 132, 136 (i.e., check for continuity) and/or the available power (i.e., voltage) of first and second batteries 130, 134. Since proximal edge 184 of removable tab 182 is not raised, proximal end 198 of rocker switch 138 is permitted to be depressed or tilted even if removable tab 182 is positioned within housing 102. As such, the status check of batteries 130, 134 may be performed with removable tab 182 positioned within housing 102 so that the status may be checked prior to operation and use of delivery system 100. Indicator light 193 (best shown in FIG. 10 in which rocker switch 138 is shown in phantom) extends through a channel of rocker switch 138 so as to be visible to the user from an exterior of housing 103. Indicator light 193 lights up when first and/or second batteries 130, 134 are functioning properly to power first and/or second motors 132, 136. Stated another way, indicator light 193 is configured to be lit when the status of first and/or second batteries 130, 134 indicates that at least one of first and second batteries first and/or second batteries 130, 134 have sufficient power to power at least one of first and second motors 132, 136. As such, the operator can ensure that at least one of first and/or second batteries 130, 134 are functioning properly to power first and/or second motors 132, 136 and sheath retraction mechanism 105 is operational. As described above, if both first and/or second batteries 130, 134 and first and second motors 132, 136 are functioning properly, outer sheath 104 may be proximally retracted faster than if only one of first and second motors 132, 136 or first and/or second batteries 130, 134 is functioning properly. However, only one motor is required to retract outer sheath 104 and thus sheath retraction mechanism 105 operates despite one motor or battery malfunctioning. The dual motors thus provide a back-up motor to ensure operation of sheath retraction mechanism 105.

A safety locking feature of actuator 138 will be described in more detail with additional reference to FIG. 12. When removable tab 182 is slidingly disposed within housing 102, it is accessible from an exterior of housing 103 of handle 102. Removable tab 182 is disposed within handle 102 until such time that delivery system 100 is to be operated. As described above, removable tab 182 does not prevent proximal end 198 of actuator or rocker switch 138 from being moved in the first or downward direction (i.e., pressing proximal end 198 thereof down) to perform a status check of first and second batteries 130, 134 when removable tab 182 is slidingly disposed within housing 103. However, the presence of removable tab 182 prevents distal end 196 of actuator or rocker switch 138 from being moved in the first or downward direction (i.e., pressing distal end 196 down) when removable tab 182 is slidingly disposed within housing 103. More specifically, raised distal edge 186 of removable tab 182 is configured to prevent distal end 196 of rocker switch from being moved or pressed down when removable tab 182 is slidingly disposed within housing 103 of handle 102. Raised distal edge 186 of removable tab 182 has a height or dimension such that raised distal edge 186 contacts level portion 195 of distal connector 194, and thereby functions as a wedge that prevents depression of lever portion 195 and in turn, distal end 196 of rocker switch 138.

Figure 12:
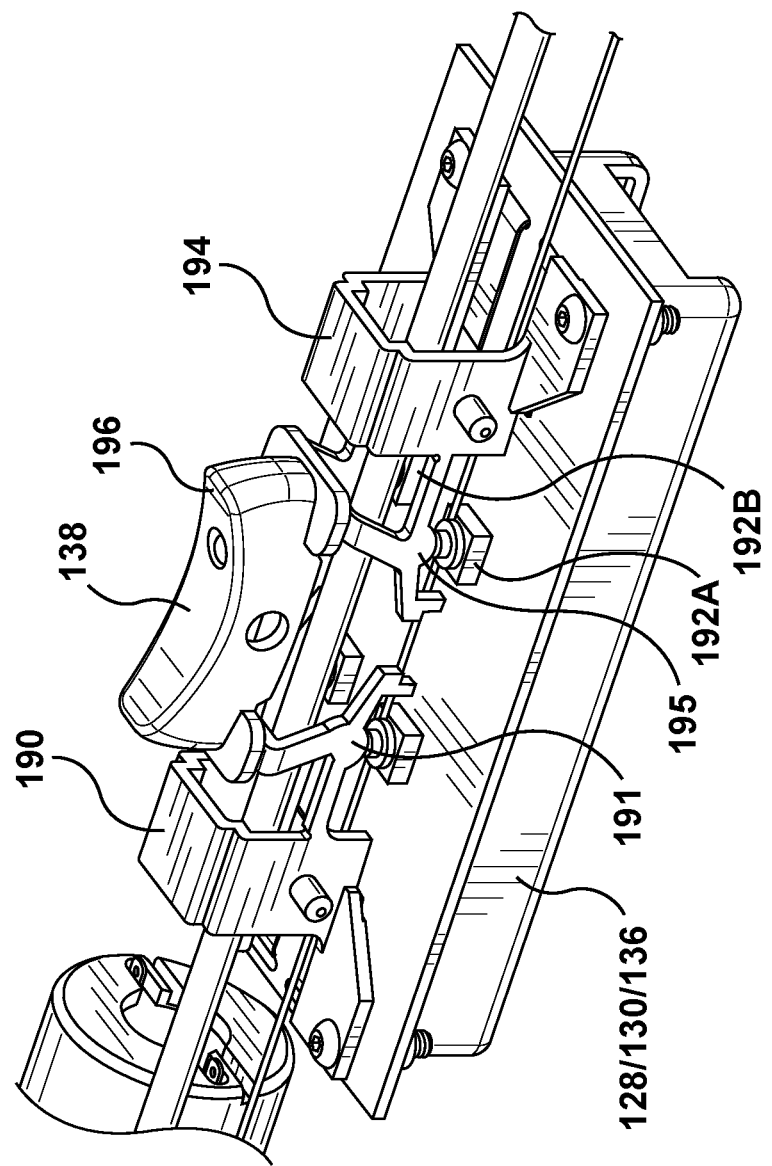
FIG. 12 is a perspective enlarged view of an actuator and the first and second batteries of the handle of the delivery system of FIG. 1, wherein the housing of the handle and the removable tab of the handle have been removed for illustrative purposes.

When it is desired to use delivery system 100, removable tab 182 may be removed from handle 102 as shown in FIG. 12. With removable tab 182 removed, when actuator or rocker switch 138 is actuated such that distal end 136 is depressed or moved in a downward direction, distal end 136 of rocker switch 138 moves or depresses lever portion 195 of distal connector 194 such that lever portion 195 contacts and activates third and fourth switches 192A, 192B. Third and fourth switches 192A, 192B are electrically coupled to first and second batteries 130, 134 such that when activated first and second motors 132, 136 simultaneously rotate (assuming batteries 130, 166 and motors 132, 136 are all functioning properly), thereby causing both first and second pulleys 150, 160 to wind up single continuous cable 140 and retract outer sheath 102 as described above.

FIGS. 13-20 illustrate a delivery system 1300 according to another embodiment hereof. As will be explained in more detail herein, delivery system 1300 is configured such that a user may select whether to retract an outer sheath 1304 thereof with one motor at a first speed or to retract outer sheath 1304 with two motors at a second speed, which is faster than the first speed. As such, the user may select to retract outer sheath 1304 at a slower rate when desirable, i.e., during the initial stages of retraction when the positioning of prosthesis 101 may still need to be adjusted, and may then select to retract outer sheath 1304 at a faster rate when desirable, i.e., during the later stages of retraction when positioning of prosthesis 101 no longer needs to be adjusted. For example, it may be desirable to retract outer sheath 1304 at a slower rate prior to tip release via a tip capture mechanism 1324 and then retract outer sheath 1304 at a faster rate after tip release via tip capture mechanism 1324. As shown on FIGS. 13-14, delivery system 1300 includes a rotatable tab or flag 1358 which provides a visual indicator for the user when outer sheath 104 has been retracted a predetermined amount. More particularly, when outer sheath 104 has been retracted to rotatable tab or flag 1358, an anchor 1366 attached to a proximal end 1306 of outer sheath 1304 contacts flag 1358 and causes it to rotate or pop up so as to extend out of housing 103 of handle 102. The location of flag 1358 is chosen so that it indicates to the user to activate tip capture mechanism 1324. For example, flag 1358 may pop up after sheath retraction mechanism 105 is operated to retract outer sheath 104 in a proximal direction such that distal end 108 no longer covers or extends over the proximal end of prosthesis 101 as described above with respect to tip capture mechanism 124. The extension or popping up of flag 1358 provides a pause during retraction of outer sheath 104 and thereby gives the user a final opportunity to adjust the position of prosthesis 101. As such, a user may retract outer sheath 1304 at a slower rate (with only one motor of delivery system 1300) prior to tip release via tip capture mechanism 1324, flag 1358 indicates timing for tip release, and then the user may retract outer sheath 1304 at a faster rate (with both motors of delivery system 1300) after the first step or stage of tip release has been performed.

Figure 13:
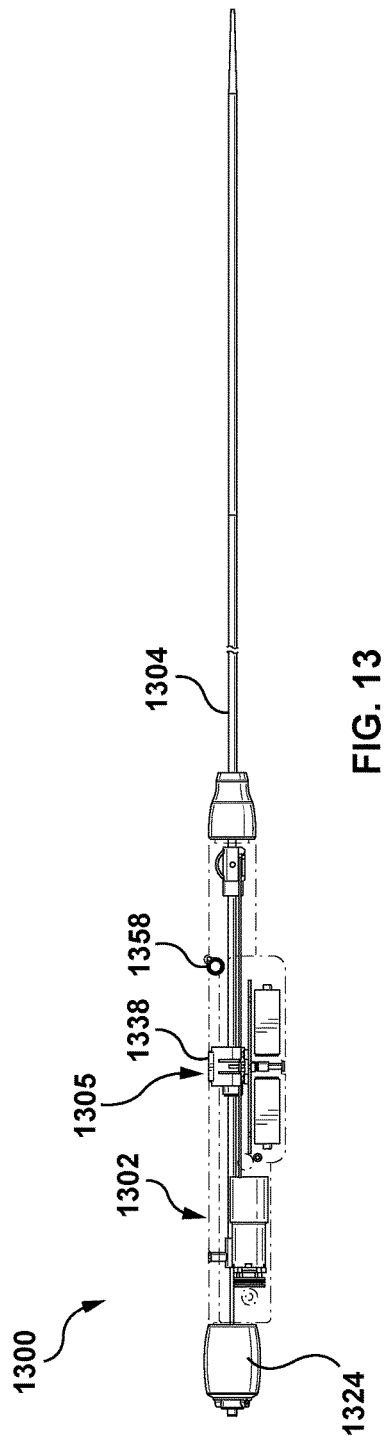
FIG. 13 is a side view of a delivery system according to another embodiment hereof, wherein an outer sheath of the delivery system surrounds and constrains a prosthesis in a compressed or delivery configuration.
Figure 14:
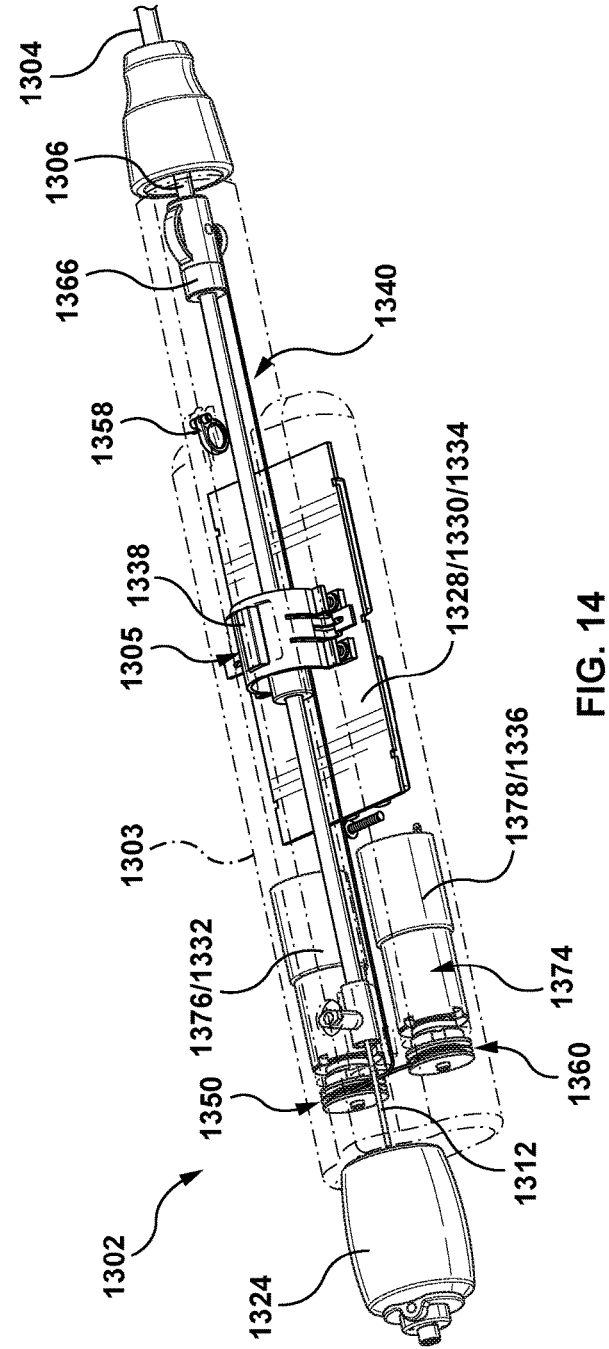
FIG. 14 is a perspective enlarged view of the handle of the delivery system of FIG. 13, wherein a housing of the handle is shown in phantom for illustrative purposes.

FIG. 13 is a side view of delivery system 1300 with outer sheath 1304 surrounding and constraining prosthesis 101 in a compressed or delivery configuration, while FIG. 14 is a perspective enlarged view of a handle 1302 of delivery system 1300, wherein a housing 1303 of handle 1302 is shown in phantom to illustrate the internal components of handle 1302. Similar to delivery system 100, delivery system 1300 also includes an inner shaft 1312 and both outer sheath 1304 and inner shaft 1312 extend from within housing 1303 of handle 1302. Outer sheath 1304 and inner shaft 1312 are the same as outer sheath 104 and inner shaft 112, respectively, described above. Handle 1302 includes tip capture mechanism 1324, which is the same as tip capture mechanism 124 as described above with respect to FIG. 3. Handle 1302 further includes a sheath retraction mechanism 1305 for retracting outer sheath 1304 as will be explained in more detail herein with respect to FIGS. 15-20. A proximal end 1306 of outer sheath 1304 is operably coupled to sheath retraction mechanism 1305 of handle 1302 and during deployment of prosthesis 101, sheath retraction mechanism 1305 is operated via an actuator 1338 accessible from an exterior of housing 1303 in order to proximally retract outer sheath 1304 to thereby incrementally expose prosthesis 101 and, once prosthesis 101 is properly positioned, to permit the full release of prosthesis 101 from delivery system 1300, as explained in more detail below.

Sheath retraction mechanism 1305 for retracting outer sheath 1204 will now be described in more detail with respect to FIGS. 14-20. Similar to sheath retraction mechanism 105, sheath retraction mechanism 1305 includes a first motor 1332 housed within housing 1303 of handle 1302 and a second motor 1336 housed within housing 1303 of handle 1302 for retracting outer sheath 1304. A mount 1374 includes a first tubular portion 1376 for receiving first motor 1332 and a second tubular portion 1378 for receiving second motor 1336. In this embodiment, a connector between the first and second tubular portions of mount 1374 is not required. First and second motors 1332, 1336 are selectively actuated for proximally retracting outer sheath 1304 in order to deploy or release prosthesis 101, thereby allowing prosthesis 101 to self-expand to a deployed or expanded configuration. In addition to first and second motors 1332, 1336, housing 1303 of handle 1302 also houses a first battery 1330 coupled to first motor 1332 for powering the first motor, and a second battery 1334 coupled to second motor 1336 for powering the second motor. Actuator 1338 is coupled to first and second batteries 1330, 1334 to selectively activate the first and second batteries to power first and second motors 1332, 1336, respectively. As described in more detail herein, in this embodiment first and second motors 1332, 1336 are configured to be selectively operated in two modes. In a first mode, only one of first and second motors 1332, 1336 rotates, thereby retracting outer sheath 1304 at a first speed. In a second mode, both first and second motors 1332, 1336 simultaneously rotate, thereby retracting outer sheath 104 at a second speed. With both first and second motors 1332, 1336 rotating, the second speed is faster or quicker than the first speed. Further, when in the second mode in which both first and second motors 1332, 1336 rotate, if one of first and second motors 1332, 1336 (or one of first and second batteries 1330, 1334, respectively) fail to operate, sheath retraction mechanism 1305 is configured to retract outer sheath 1304 with only one operating motor (i.e., the other of first and second motors 1332, 1336). Stated another way, sheath retraction mechanism 1305 still operates to retract outer sheath 1304 if one of first and second motors 1332, 1336 malfunctions or if one of first and second batteries 1330, 1334 does not have sufficient charge to power its respective motor.

Figure 15:
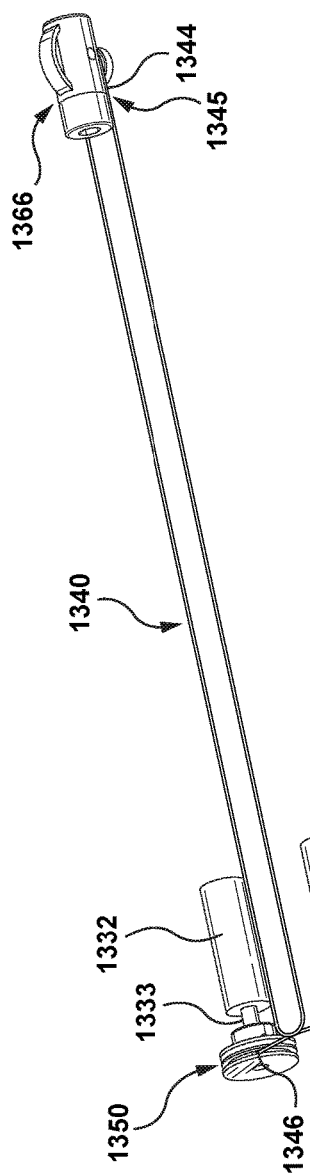
FIG. 15 is a perspective view of select components of the handle of the delivery system of FIG. 13 to illustrate a single continuous cable of the handle of the delivery system of FIG. 13, wherein the other components of the handle have been removed for illustrative purposes.

FIG. 15 is a perspective view of select components of handle 1302 to illustrate operation of first and second motors 1332, 1336 with a single continuous cable 1340. Housing 1303 and various other components of the handle have been removed to isolate components described in relation to FIG. 15. In addition to first and second motors 1332, 1336 and their respective first and second batteries 1330, 1334, sheath retraction mechanism 1305 further includes single continuous cable 1340 having a first end 1346 coupled to a first pulley 1350, a second end 1348 coupled to a second pulley 1360, and an intermediate portion 1345 coupled to proximal end 1306 of outer sheath 1304. As best shown in FIG. 15, intermediate portion 1345 of single continuous cable 1340 coupled to proximal end 1306 of outer sheath 1304 via an anchor 1366 which is similar to anchor 166. Intermediate portion 1345 of single continuous cable 1340 includes a distal loop 1344 that extends through a passageway (not shown in FIG. 15) of anchor 1366 in order to couple the intermediate portion of the single continuous cable to proximal end 1306 of outer sheath 1304. Similar to single continuous cable 140, single continuous cable 1340 may be formed from any sufficiently strong suitable material, including but not limited to Kevlar® or other suitable synthetic fiber.

Figure 16:
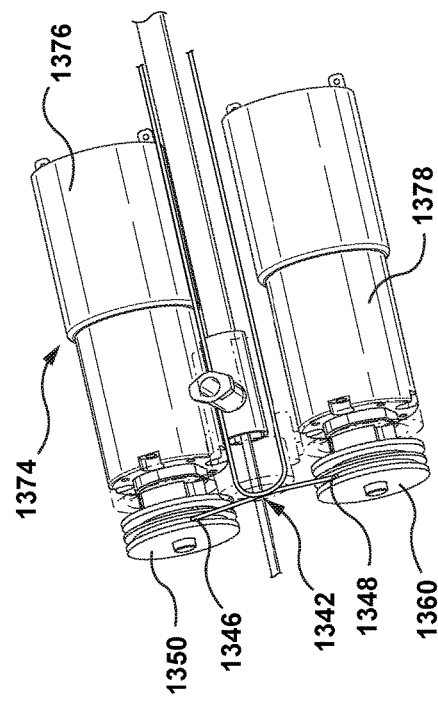
FIG. 16 is a perspective enlarged view of the handle of the delivery system of FIG. 13, wherein the housing of the handle has been removed to illustrate placement of the single continuous cable of the handle of the delivery system of FIG. 13.

FIG. 16 is a perspective enlarged view of handle 1302 with housing 1303 removed to illustrate placement of single continuous cable 140 proximate to first and second pulleys 1350, 1360. The portion of single continuous cable 140 proximate to first tubular portion 1376 of mount 1374 extends to second pulley 1360 such that second end 1348 of single continuous cable 140 is attached to second pulley 1360. Conversely, the portion of single continuous cable 140 proximate to second tubular portion 1378 of mount 1374 extends to first pulley 1350 such that first end 1346 of single continuous cable 140 is attached to first pulley 1350. As a result, the two portions of single continuous cable 140 proximate to first and second pulleys 1350, 1360 include a crossover or intersection portion 1342 as best shown in FIG. 16 in which the two portions of single continuous cable 140 proximate to first and second pulleys 1350, 1360 overlap or overlay each other. As such, single continuous cable 1340 is an elongated element with first end 1346 coupled to first pulley 1350, second end 1348 coupled to second pulley 1360, and the length of single continuous cable 1340 is looped around anchor 1366. Utilizing a single continuous cable that winds around both first and second pulleys 1350, 1360 rather than two separate cables provides a mechanical advantage that amplifies the force applied for retracting outer sheath 1304. For example, in an embodiment, the force output by a single continuous cable that winds around both first and second pulleys 1350, 1360 may be twice as much as a force output by a system that uses two pulleys each having a separate cable attached thereto for retracting outer sheath 1304.

As best shown in FIGS. 14 and 15, first pulley 1350 is directly coupled to a motor shaft 1333 of first motor 1332 such that first pulley 150 rotates during operation of first motor 132. Similarly, second pulley 1360 is directly coupled to a motor shaft 1337 of second motor 1336 such that second pulley 1360 rotates during operation of second motor 1336. Thus, in this embodiment, bevel gears are eliminated and first and second pulleys 1350, 1360 are directly coupled to first and second motors 1332, 1336. First and second pulleys 1350, 1360 are collinear with first and second motors 1332, 1336. In the depicted embodiment, each of first and second pulleys 1350, 1360 are single-groove pulleys that each include a circumferential groove or channel formed on an outer surface thereof for receiving cable 1340. As will be understood by one of ordinary skill in the art, the diameter of first and second pulleys 1350 1360 may vary from that shown and may vary from each other depending upon the desired speed of retraction.

First and second motors 1332, 1336 are configured to rotate in opposing directions. For example, first motor 1332 (and first pulley 1350 directly coupled thereto) rotates in a first or clockwise direction and second motor 1336 (and second pulley 1360 directly coupled thereto) rotates in a second or counter-clockwise direction. In another example, first motor 1332 (and first pulley 1350 directly coupled thereto) rotates in a counter-clockwise direction and second motor 1336 (and second pulley 1360 directly coupled thereto) rotates in a clockwise direction. In this embodiment, first and second pulleys 1350, 1360 are configured to be rotated independently of each other. More particularly, as described above, first and second motors 1332, 1336 are configured to be selectively operated in two modes. In a first mode in which only one of first and second motors 1332, 1336 rotates, only the corresponding pulley (i.e., first or second pulley 1350, 1360, respectively) rotates to wind up a portion of single continuous cable 1340. When only one of first and second pulleys 1350, 1360 rotate, a portion of single continuous cable 1340 winds around the rotating pulley (one of first and second pulleys 1350, 1360) and outer sheath 1304 is proximally retracted at a relatively slower rate. In a second mode in which both first and second motors 1332, 1336 rotate, both corresponding pulleys (i.e., first and second pulley 1350, 1360) rotate to wind up a portion of single continuous cable 1340. When both first and second pulleys 1350, 1360 rotate, a portion of single continuous cable 1340 winds around each of first and second pulleys 1350, 1360 and outer sheath 1304 is proximally retracted at a relatively faster or quicker rate. Thus, in this embodiment, first and second pulleys 1350, 1360 only rotate when the corresponding motor (first or second motor 1332, 1334, respectively) rotates. Stated another way, first and second pulley 1350, 1360 are configured to be rotated independently with rotation of first and second motors 1332, 1336, respectively.

Actuation of actuator 1338, which selectively causes either one or both of first and second motors 1332, 136 to rotate, will now be described in more detail with reference to FIGS. 17-18. FIG. 17 is a perspective enlarged view of actuator 1338 and first and second batteries 1330, 1334, and housing 1303 of handle 1302 has been removed for illustrative purposes. Actuator 1338 is a rocker switch that is configured to move or tilt side-to-side in first and second opposing directions in this embodiment. Actuator 1338 is a semi-circular component having a first lever arm 1391 at a first side and a second lever arm 1395 at a second opposing side. First and second lever arms 1391, 1395 are configured to contact an outer surface of a battery housing 1328 and thereby center rocker switch 1338 thereon. First and second lever arms 1391, 1395 are configured to permit rocker switch 1338 to be tilted or moved in a first direction towards first lever arm 1391 and a second opposing direction towards lever arm 1395. Rocker switch 1338 further includes four legs, first and second legs 1390A, 1390B and third and fourth legs 1394A, 1394B. First and second legs 1390A, 1390B extend on either side of first lever arm 1391 and third and fourth legs 1394A, 1394B extend on either side of second lever arm 1395. First and second legs 1390A, 1390B and third and fourth legs 1394A, 1394B each have a length shorter than first and second lever arms 1391, 1395, respectively, so that the ends thereof do not contact the outer surface of battery housing 1328 without force applied thereto. First and second legs 1390A, 1390B and third and fourth legs 1394A, 1394B are movable with respect to battery housing 1328.

Handle 1302 also includes first and second switches 1388A, 1388B and third and fourth switches 1392A, 1392B. First and second switches 1388A, 1388B and third and fourth switches 1392A, 1392B are all electrically coupled to first and second batteries 1330, 1334 as will be described in more detail herein. First and second legs 1390A, 1390B of rocker switch 1338 are axially aligned with first and second switches 1388A, 1388B, while third and fourth legs 1394A, 1394B are axially aligned with third and fourth switches 1392A, 1392B. When actuator or rocker switch 1338 is actuated in the first direction towards first lever arm 1391 such that first and second legs 1390A, 1390B are depressed or moved in a downward direction, one of first and second motors 1332, 1336 rotates, thereby causing the respective one of first and second pulleys 1350, 1360 to wind up single continuous cable 1340 and retract outer sheath 1304 at a relatively slow speed as described above. When actuator or rocker switch 1338 is actuated in the second opposing direction towards lever arm 1395 such that third and fourth legs 1394A, 1394B are depressed or moved in a downward direction, both of first and second motors 1332, 1336 rotate (assuming batteries 1330, 1334 and motors 1332, 1336 are all functioning properly), thereby causing both first and second pulleys 1350, 1360 to wind up single continuous cable 1340 and retract outer sheath 1304 at a relatively fast or quick speed as described above.

The embodiment of FIGS. 13-20 includes a check status feature as well in the form of a second actuator or button 1357. FIG. 19 is a bottom view of a portion of handle 1302, wherein housing 1303 of handle 1302 is shown in phantom for illustrative purposes. FIG. 20 is a perspective exploded view of button 1357 and surrounding components of handle 1302, wherein the housing 1303 of handle 1302 is removed for illustrative purposes. As shown in FIG. 19, second actuator or button 1357 is accessible from an exterior of housing 1303 of handle 1302. When pressed, button 1357 is configured to check a status of first and second batteries 1330, 1334 prior to operation and use of delivery system 100. When button 1357 is pressed or moved in an upward direction, it contacts and activates a fifth switch 1359. Fifth switch 1359 is electrically coupled to first and second batteries 1330, 1334 such that when activated a status check of first and second batteries 1330, 1334 is performed but neither first and second motors 1332, 1336 rotate. Although not shown in this embodiment, an indicator light may be included and configured to light up when first and/or second batteries 1330, 1334 are functioning properly to power first and/or second motors 1332, 1336. As such, the operator can ensure that at least one of first and/or second batteries 1330, 1334 are functioning properly to power first and/or second motors 1332, 1336 and sheath retraction mechanism 1305 is operational. As described above, if both first and/or second batteries 1330, 1334 and first and second motors 1332, 1336 are functioning properly, outer sheath 1304 may be proximally retracted faster than if only one of first and second motors 1332, 1336 or first and/or second batteries 1330, 1334 is functioning properly. However, only one motor is required to retract outer sheath 1304 and thus sheath retraction mechanism 1305 operates despite one motor or battery malfunctioning. The dual motors thus provide a back-up motor to ensure operation of sheath retraction mechanism 1305.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A delivery system for delivering a prosthesis, the delivery system comprising:
    a housing;
    a sheath extending from within the housing;
    a first motor housed within the housing;
    a first battery coupled to the first motor for powering the first motor, the first battery housed within the housing;
    a second motor housed within the housing;
    a second battery coupled to the second motor for powering the second motor, the second battery housed within the housing;
    an actuator accessible from an exterior of the housing, wherein the actuator is coupled to the first and second batteries to selectively activate the first and second batteries to power the first and second motors, respectively; and
    a single continuous cable having a first end coupled to a first pulley and a second end coupled to a second pulley, the first pulley being coupled to the first motor such that the first pulley rotates during operation of the first motor and the second pulley being coupled to the second motor such that the second pulley rotates during operation of the second motor, wherein an intermediate portion of the single continuous cable is coupled to a proximal portion of the sheath and actuation of the actuator causes at least one of the first and second motors to rotate, thereby causing at least one of the first and second pulleys to wind up a portion of the single continuous cable and retract the sheath.

2. The delivery system of claim 1, wherein an anchor is attached to the proximal portion of the sheath and the intermediate portion of the single continuous cable is looped through a passageway formed in the anchor in order to couple the intermediate portion of the single continuous cable to the proximal portion of the sheath.

3. The delivery system of claim 2, wherein a second intermediate portion of the single continuous cable is looped around a portion of a mount that holds the first and second motors.

4. The delivery system of claim 1, wherein the actuator includes a rocker switch.

5. The delivery system of claim 4, wherein the rocker switch has a proximal end and a distal end that are each configured to be moved in a first direction and wherein actuation of the proximal end of the rocker switch in the first direction checks a status of the first and second batteries but does not cause either of the first and second motors to rotate, and actuation of the distal end of the rocker switch in the first direction causes both the first and second motors to rotate, thereby causing both the first and second pulleys to wind up a portion of the single continuous cable and retract the sheath.

6. The delivery system of claim 5, further comprising:
a removable tab slidingly disposed within the housing and accessible from an exterior of the housing, wherein the removable tab prevents the distal end of the rocker switch from being moved in the first direction when the removable tab is slidingly disposed within the housing.

7. The delivery system of claim 6, wherein the removable tab includes a raised edge around a portion of a perimeter thereof, the raised edge being configured to prevent the distal end of the rocker switch from being moved in the first direction when the removable tab is slidingly disposed within the housing.

8. The delivery system of claim 6, wherein the removable tab does not prevent the rocker switch from being moved in the first direction when the removable tab is slidingly disposed within the housing.

9. The delivery system of claim 4, further comprising an indicator light housed within the housing, wherein the indicator light is configured to be lit when the status of the first and second batteries indicates that at least one of the first and second batteries have sufficient power to power at least one of the first and second motors.

10. The delivery system of claim 1, wherein the first and second pulleys are configured to be rotated simultaneously with rotation of either the first or second motor.

11. The delivery system of claim 4, wherein the rocker switch is configured to be moved in a first direction and a second direction and wherein actuation of the rocker switch in the first direction causes one of the first and second motors to rotate, thereby causing one of the first and second pulleys to wind up a portion of the single continuous cable and retract the sheath at a first speed, and actuation of the rocker switch in the second direction causes both the first and second motors to rotate, thereby causing both the first and second pulleys to wind up a portion of the single continuous cable and retract the sheath at a second speed, the second speed being faster than the first speed.

12. The delivery system of claim 11, further comprising:
a second actuator accessible from an exterior of the housing, the second actuator configured to check a status of the first and second batteries.

13. The delivery system of claim 1, wherein the first and second pulleys are configured to be rotated independently with rotation of the first and second motors, respectively.

14. A delivery system for delivering a prosthesis, the delivery system comprising:
a housing;
a sheath extending from within the housing;
a first motor housed within the housing;
a first battery coupled to the first motor for powering the first motor, the first battery housed within the housing;
a second motor housed within the housing;
a second battery coupled to the second motor for powering the second motor, the second battery housed within the housing;
an actuator accessible from an exterior of the housing, wherein the actuator is coupled to the first and second batteries to selectively activate the first and second batteries to power the first and second motors, respectively; and
at least one cable coupled to a first pulley and to a second pulley, the first pulley being coupled to the first motor such that the first pulley rotates during operation of the first motor and the second pulley being coupled to the second motor such that the second pulley rotates during operation of the second motor, wherein the at least one cable is coupled to a proximal portion of the sheath and actuation of a proximal end of the actuator checks a status of the first and second batteries, and actuation of a distal end of the actuator causes both the first and second motors to rotate, thereby causing both the first and second pulleys to wind up a portion of the at least one cable and retract the sheath.

15. The delivery system of claim 14, further comprising:
a removable tab slidingly disposed within the housing and accessible from an exterior of the housing, wherein the removable tab prevents the distal end of the actuator from being moved when the removable tab is slidingly disposed within the housing.

16. The delivery system of claim 15, wherein the removable tab includes a raised edge around a portion of a perimeter thereof, the raised edge being configured to prevent the distal end of the actuator from being moved when the removable tab is slidingly disposed within the housing.

17. The delivery system of claim 15, wherein the removable tab does not prevent the proximal end of the actuator from being moved when the removable tab is slidingly disposed within the housing.

18. The delivery system of claim 14, further comprising an indicator t housed within the housing, wherein the indicator light is configured to be lit when the status of the first and second batteries indicates that at least one of the first and second batteries have sufficient power to power at least one of the first and second motors.

19. A delivery system for delivering a prosthesis, the delivery system comprising:
a housing;
a sheath extending from within the housing;
a first motor housed within the housing;
a first battery coupled to the first motor for powering the first motor, the first battery housed within the housing;
a second motor housed within the housing;
a second battery coupled to the second motor for powering the second motor, the second battery housed within the housing;
an actuator accessible from an exterior of the housing, wherein the actuator is coupled to the first and second batteries to selectively activate the first and second batteries to power the first and second motors, respectively; and
at least one cable coupled to a first pulley and to a second pulley, the first pulley being coupled to the first motor such that the first pulley rotates during operation of the first motor and the second pulley being coupled to the second motor such that the second pulley rotates during operation of the second motor, wherein the at least one cable is coupled to a proximal portion of the sheath and actuation of the actuator in a first direction causes one of the first and second motors to rotate, thereby causing one of the first and second pulleys to wind up a portion of the at least one cable and retract the sheath at a first speed, and actuation of the actuator in a second direction causes both the first and second motors to rotate, thereby causing both the first and second pulleys to wind up a portion of the at least one cable and retract the sheath at a second speed, the second speed being faster than the first speed.

20. The delivery system of claim 19, wherein the first and second pulleys are configured to be rotated independently with rotation of the first and second motors, respectively.

* * * * *